United States Patent [19]

Saliba, Jr.

[11] Patent Number: 5,037,810

[45] Date of Patent: Aug. 6, 1991

[54] MEDICAL APPLICATION FOR HEPARIN AND RELATED MOLECULES

[76] Inventor: Michael J. Saliba, Jr., 5582 Thunderbird La., La Jolla, Calif. 92037

[21] Appl. No.: 412,403

[22] Filed: Sep. 26, 1989

Related U.S. Application Data

[62] Division of Ser. No. 27,195, Mar. 17, 1987, Pat. No. 4,879,282.

[51] Int. Cl.$^5$ .......................................... A61K 31/725
[52] U.S. Cl. ....................................... 514/56; 514/54; 514/863; 514/928
[58] Field of Search ................... 514/54, 56, 863, 928

[56] References Cited

U.S. PATENT DOCUMENTS

| | | | |
|---|---|---|---|
| 3,062,716 | 11/1962 | Montandraud | 514/56 |
| 3,232,833 | 1/1966 | Riviere | 514/56 |
| 3,636,202 | 1/1972 | Klein | 514/56 |
| 4,745,098 | 5/1988 | Michaeli | 514/56 |
| 4,760,131 | 7/1988 | Sunosmo et al. | 514/56 |
| 4,808,570 | 2/1989 | Michaeli | 514/56 |

FOREIGN PATENT DOCUMENTS

| | | |
|---|---|---|
| 0154447 | 9/1985 | European Pat. Off. . |
| 2101393 | 9/1971 | Fed. Rep. of Germany . |
| 0850082 | 7/1981 | U.S.S.R. . |
| 0997639 | 2/1983 | U.S.S.R. . |
| 1033141 | 8/1983 | U.S.S.R. . |
| 1069816 | 1/1984 | U.S.S.R. . |
| 1097335 | 6/1984 | U.S.S.R. . |
| 8705808 | 10/1987 | World Int. Prop. O. . |

OTHER PUBLICATIONS

Dyurd: Annals of Dermatology And Venerology 3:69 ∝ 70 (1978).
Novotny; Acta Univ. Carol. Med. 31(3/4): 243-245 (1985).
Nissenson et al., Annals of Internal Medicine 91(2):218-220, (1979).
Jespersen et al., The Lancet 2(8462): 1010-1011 (11-2-85).
Saliba, Jr. et al., J.A.M.A. 225(3):261-269 (1973).
Casu, Adv. Carb. Chem. Biochem. 43:127-134 (1985).
Ingber et al. In Vitro Cell. Dev. Biol. 23(5):387-394, May 1987,

*Primary Examiner*—Ronald W. Griffin
*Assistant Examiner*—Nancy S. Carson
*Attorney, Agent, or Firm*—Brown, Martin Haller and McClain

[57] ABSTRACT

New uses for heparin, or heparin-like compounds are described that encompass preserving and healing of cells and cell functions arising from transplantations, circumcisions, dermatitides, fissures, fistulas, stimulation of epithelial growth, keloid prevention, cold injuries, pathology and forensic diagnosis, myocardium, trauma, decubitus ulcers, psoriasis, poisonings, insect and snake bites, corrosive ingestions, the "bends," space-travel sickness, brain and heart nerve conduction electrical dysrhythmias, pulmonary respiratory distress, blood and blood products, ulcerative colon lesions, interstitial cystitis, and related cosmetic uses. The uses are realized by applying the compounds either in solution, or in the for of a cream or aerosol, preferably at a pH of about 5.5, in an effective amount and for a time sufficient to effect treatment. Generally, the concentration of heparin or heparin-like compounds will be in the range of 1500 to 5000 international units per milliliter. Clinical assays are also described for determining the amount of heparin that should be used in those instances where the effective concentration is not known.

18 Claims, 6 Drawing Sheets

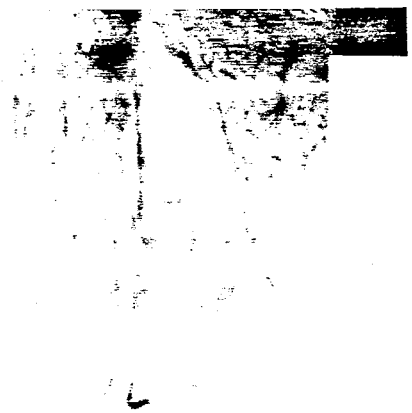
FIG. 1A
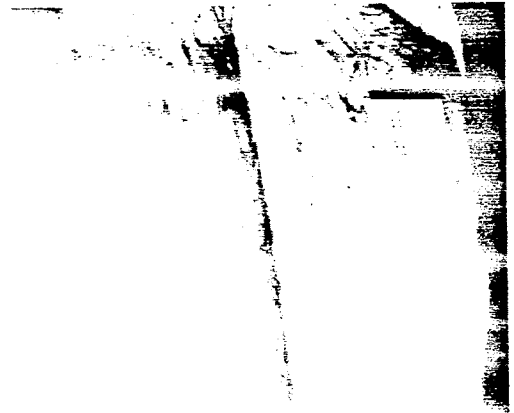
FIG. 1B
FIG. 1C
FIG. 1D

BEST AVAILABLE COPY

BEST AVAILABLE COPY
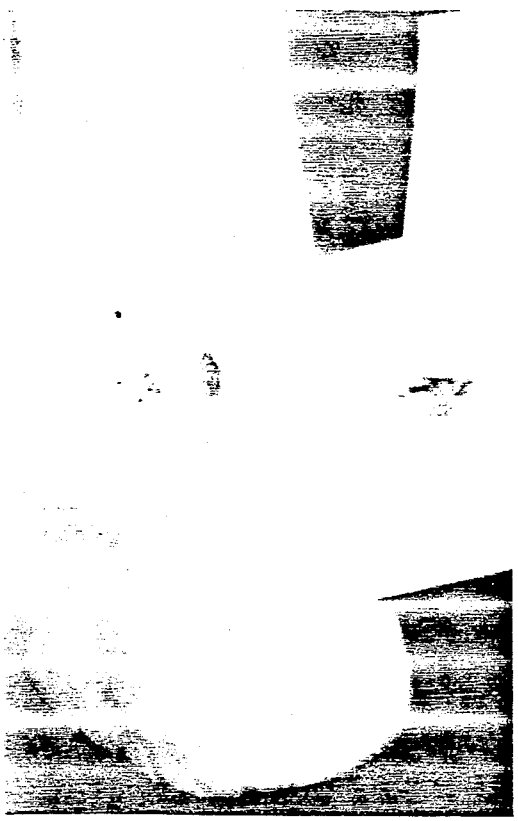
FIG. 2E
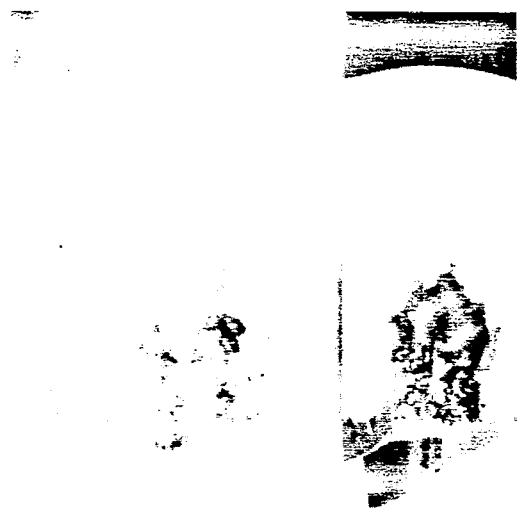
FIG. 2F
FIG. 2G
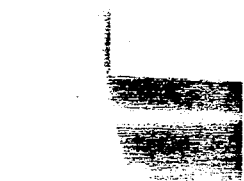
FIG. 2H

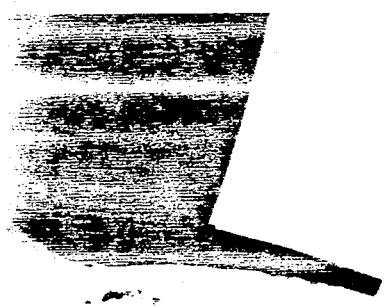
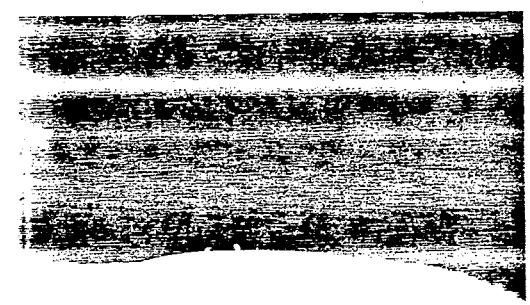
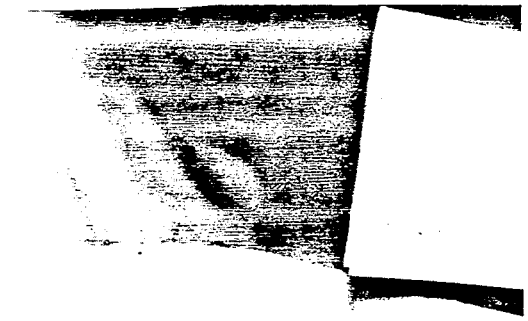
FIG. 3A  FIG. 3B  FIG. 3C  FIG. 3D

BEST AVAILABLE COPY

MEDICAL APPLICATION FOR HEPARIN AND RELATED MOLECULES

CROSS-REFERENCE TO RELATED APPLICATIONS

This application is a divisional of Ser. No. 07/027,195 filed Mar. 17, 1987 and issued Nov. 7, 1989, as U.S. Pat. No. 4,879,282.

BACKGROUND OF THE INVENTION

Heparin is a polysaccharide present in a variety of organs and tissues, particularly liver, lung, and the large arteries. It is a polymer of repeating units of D-glucuronic acid usually having an O-sulfate group at C-2 and D-glucosamine N-sulfate with an additional O-sulfate group at C-6. Both the linkages of the polymer are alternating -1,4, and it is thought that seven of the eight glucuronic acid residues in the polymer exhibit an O-sulfate group. The postulated repeating unit is shown as follows:

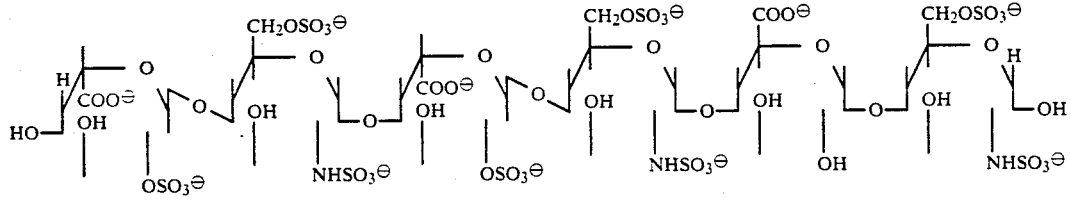

as defined by Jaques, *Science*, 206, 529 (1979) and Rawn, *Biochemistry*, 297-298 (1983). Heparin is commonly provided as the sodium salt, sometimes referred to as sodium heparinate or heparin sodium, as indicated in U.S. Pat. No. 3,062,716 (Montaudraud) and as "Entry 4543" in *The Merck Index*, 672 (10th edn., 1983).

One of the major properties of heparin which has been recognized for some time is its ability to prolong the clotting time of blood both in vivo and in vitro. Less well known properties of heparin are that it stimulates healing of burn wounds and its ability to reverse ischemic myocardial injuries. For instance, Saliba et al. in *J. Amer. Med. Assoc.*, 225, 261 (1973) describe the application of heparin administered parenterally and topically to humans suffering from second and third degree burns. Heparin both relieves the pain and prevents the initial burn size from expanding. Most important, there is enhanced revascularization, granulation and re-epithelialization. The effect of heparin on burn wound healing is critically dose-related, dose dependent and pH regulated (Saliba, *Thrombosis and Haemostasis*, 40, No. 1 (1978). Most applications of heparin as a therapeutic agent have used concentrations in the range of 20,000 to 40,000 units/per milliliter for intravenous or subcutaneous modes of presentation, while for topical applications concentrations in the range of 5,000 to 10,000 units/per milliliter have been employed. The beneficial effect of heparin on reversing myocardial ischemic injury generally has been shown to require the administration of 10,000 to 100,000 units total of 5,000 to 10,000 units/ml heparin, with favorable results being apparent acutely on electrocardiograms and on cardiac enzymes monitored at 24 and 48 hours.

In addition to the above effects of heparin, the molecule is also thought to exhibit antithrombin, antiplatelet-lysis, thrombolytic, antihistaminic, antiserotonin and antiproteolytic enzymatic activity. The mechanism whereby heparin exerts all these effects is not known. Lastly, heparin has also been shown to be effective in treating weeping poison oak dermatitis (Saliba and Griner, *Aerospace Medicine*, 41, 2, 179 (1970)) and weeping ear eczema and acute tracheal bronchitis (Dougherty and Dolowitz, *Amer. J. Cardiol*, 14., 18 (1964)).

The following U.S. patents show various medical applications for heparin or related compounds. U.S. Pat. No. 3,062,716 shows a method of treating hemorrhoids. U.S. Pat. No. 3,137,624 describes compositions for treating defective veins wherein one component is heparin. U.S. Pat. No. 3,244,594 describes heparin compounds having antitumor activity. U.S. Pat. No. 3,151,025 describes a composition that rids the blood of lipoprotein molecules. U.S. Pat. No. 4,039,665 shows a method of composition containing heparin for eradication of venous blemishes. Lastly, U.S. Pat. No. 4,390,532 shows another composition with heparin that is useful for topical applications in treating wrinkles, acne and androgen baldness.

SUMMARY OF THE INVENTION

It is an object of this invention to describe new uses for heparin and heparin related molecules, particularly heparin sulfate, heparin acids and the like, that rely on the hithertofore unappreciated anticellular destructive effects of these molecules. Over a well defined range of heparin concentrations and pHs, particularly acidic pH's, it is shown that there is an inhibition of cellular destruction which in turn facilitates healing of wounded cells, tissues or organs.

This patent describes a method of using heparin and heparin related substances to facilitate transplantation in humans and animals by preserving the transplant prior to removal from a donor and during transportation and surgical transplantation into the recipient. Heparin prevents cellular breakdown and destruction of the transplant, minimizes rejection and enhances physiological function of the transplant(s). This in turn obviates or reduces the need to use immunosuppressants, thereby lessening morbidity and mortality.

By transplant it will be understood that reference is made to any human or animal body part, cell, tissue or organ removed from a human or animal donor and placed for use on, or within a human or animal recipient. It is a particular object of the invention to show that because heparin and related compounds efficaciously prolong the in vitro lifetime of organs removed from transplant donors, it enables organs to be transplanted into a recipient after the organ has been out of the donor for a longer time than has been hithertofore been possible.

It is yet a further object of this invention to show that heparin and related compounds are efficacious in stimulating healing of skin wounds generally, but particularly including those arising from circumcision, cold injuries, dermatitides, fissures, fistulas, stimulation of epithelial growth, keloid prevention, cold injuries, pathology and forensic diagnosis, myocardium, trauma, decubitus ulcers, psoriasis, poisonings, insect and snake bites, corrosive ingestions, the "bends," space-travel sickness, brain and heart nerve conduction electrical dysrhythmias, pulmonary respiratory distress, blood and blood products, ulcerative colon lesions, intersititial cystitis and related cosmetic uses.

It will be understood by those skilled in the art that the scope of applications of heparin is not limited to the particular injuries described above. It is expected that it will be useful for simulating healing of virtually any tissue that requires re-epithelialization and/or revascularization when these processes are prevented or retarded from occurring due to the release of cellular chemicals exhibiting cytotoxic activity, and complicated by ischemia and infection.

BRIEF DESCRIPTION OF THE DRAWINGS

The FIGS. of the drawings are sets of photographs of the various stages of the healing process for patients treated in accordance with this invention. Each of the sets is described in, respectively, Examples I, III, VII, VIII and X.

DETAILED DESCRIPTION OF THE INVENTION

Figure 2B:
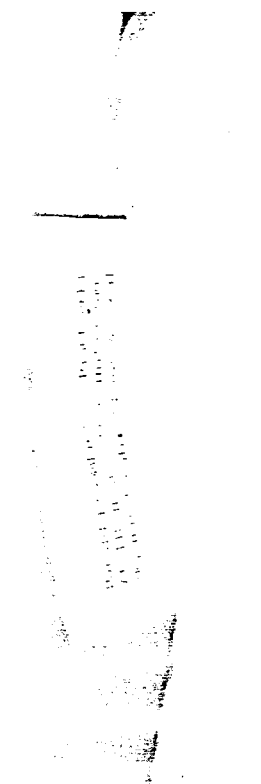

Underlying the novel uses of heparin or chemically related molecules described herein is that they are capable, under suitable conditions of pH and concentration, of retarding or preventing cellular-destructive biochemical events which are associated both with slow wound healing and with the rapid destruction of organs once removed from the body. Heparin also stimulates endothelial cell migration and proliferation in ischemic tissue. By preventing cellular and tissue destruction and by enhancing neoangiogenesis in ischemic areas it is possible to promote rapid revascularization, granulation and re-epithelialization associated with a wound and shorten healing time and improve final functional and cosmetic results. Similarly it permits organ transplants using organs that are have been removed from the donor for longer times than hithertofore possible. These two types of medical problems are the preferred, but not the only new uses that are beneficially treated with heparin.

Included within the category of skin wounds is ischemic traumatic wounds which are beneficially treated with heparin to prevent vascular necrosis until an adequate vascular supply can be re-established. An example of this type of skin wound would be a traumatic amputation.

Other ischemic applications include myocardial ischemia or injury at any stage and arrhythmias. Treatment can consist of venous infusion using a peripheral vein or the administration of heparin by an in-dwelling catheter at the base of the aorta or in coronary artery(ies) directly. The use of heparin and heparin related substances preserves ischemic myocardium which in turn preserves heart function. Heparin selectively prevents and corrects cardiac arrhythmias. Although heparin does not lyse blood clots as effectively as streptokinase and urokinase, it has multiple anticellular destructive effects not found in those chemicals that preserve and heal ischemic myocardium.

Another application of heparin is to treat circumcision wounds. The ideal concentration is 2,500 International Units/Milliliter (I.U./ml). While a variety of treatment modalities will perform satisfactorily, the preferred treatment consists of applying 0.5 ml of heparin solution directly on the penis after surgery and then applying a nonadhering dressing soaked with 1.0 ml of heparin solution to enhance healing, especially the rapid re-epithelialization of the surgically denuded glans penis and residual foreskin surfaces, and to prevent adherence and adhesion of the denuded non-healed surfaces. Currently the adhering foreskin in many boys must be repeatedly and painfully peeled off its attachment to the glans intermittently, for months or years post-circumcision, before there is proper healing. The heparin treatment can be used whenever the adhering foreskin is separated from its attachment to the glans penis surface, days, months or years after circumcision. A treatment package would contain an individual 3 ml vial of 2,500 I.U./ml sterile acidic heparin solution, a vial of sterile physiological saline water, appropriate-size nonadherent pads and a mesh circular gauze to be used by surgeons and to be provided to a patient's parents for post-circumcision care of the circumcised penis.

Another procedure that facilitates the re-epithelialization of circumcision wounds consists of topically applying heparin from intestinal mucosa in solution at about 2,500 I.U./ml immediately postcircumcision. 0.5 ml of the solution is applied on the denuded surfaces and 1.0 ml on the nonadhering bandage and 1.0 ml with each, if any, changing of the bandage into final healing. The heparin soaked nonadhering bandage dressing will be wrapped around the denuded surfaces and held in place with the circular gauze mesh dressing. Sterile water will be used to soak the old bandage prior to its removal from the healing surface to prevent disruption of the healing new epithelial surface.

Heparin protection of cellular destruction and enhancement of revascularization and heparin induced epithelialization and re-epithelialization can be favorably applied to treat dermatitides, fissures, and fistulas that are difficult to heal, or are refractory to current methods of treatment. These can be healed by the addition of heparin using the methods described for treating circumcisions wherein heparin is generally applied topically twice a day, and sometimes subcutaneously for a limited time in a limited dose. Further, heparin can be used to stimulate and facilitate in vivo re-epithelialization of diseased or injured or denuded body surfaces and in vitro for skin homografts and heterografts, as well as to inhibit or prevent the formation of keloids.

Further uses of heparin and related molecules include skin injuries due to cold temperature exposure, such as frostbite. The latter can be treated in any stage of the injury, especially prior to or during the warm-upstage, as well as in the intermediate post thawing stage and for several hours or days thereafter as needed to effect complete recovery. The use of heparin in hypothermia, as a preventive or as a treatment will reduce morbidity and mortality. This use will be invaluable to humans and animals exposed to environmental conditions where hypothermia can be life-threatening, including but not limited to mountain climbers, deep-water divers and individuals living in cold environments on earth. A self-administered subcutaneous injection of heparin, in 10,000–40,000 I.U. doses, once or twice daily, would prevent blood-clotting and cellular-destruction and preserve and maintain life. A continuous intravenous infusion could be used with the dose monitored by health personnel during medical treatment. For the final phases of recovery at home, the self-administered subcutaneous injections of 5,000 to 20,000 I.U. daily would complete the treatment.

Sunburns or thermal burns are yet another class of skin treatments that are efficaciously treated by heparin. Again, it will be appreciated that while heparin is the preferred chemical, molecules having similar activity will perform equally well.

In ongoing experiments, psoriasis has responded to treatment with heparin applied topically and parenterally and specifically is intended to come within the scope of this application.

Heparin can be beneficially utilized in the area of organ transplants as its anticellular destructive activity essentially preserves organs that have been removed from a donor for longer periods of time than has hitertofore been possible. This allows for organs, tissues or cells to be removed and then flown to virtually any region of the earth for use by a needy recipient.

An exemplary procedure for preparing an organ for transplantation may consist of first infusing the intract donor with a bolus intravenous injection of about 10,000 I.U. of heparin given just prior to initial surgery. Preferably the solution will be buffered at a pH of about 5.5. Heparin anticoagulates the donor and neutralizes cellular-destructive inflammation-producing biochemicals such as histamine, serotonin, etc. Next, surgically expose the donor part's and the transplant's, and isolate the transplant's major arteries and veins, whenever possible. Use a soft-covered surgical clamp to occlude the transplant's principal artery at its most proximal origin and the greatest distance away from its entrance into the donor part, the transplant. Using a sufficient quantity of about 1,000 I.U./ml intestinal source heparin solution or dextran solution infused through an eighteen gauze needle inserted into the artery just beyond the clamp, flush out the blood in that artery and the transplant and the exiting veins with the heparin or dextran solution until no blood remains. This will prevent intra-transplant clotting of blood and the pathological sequellae of micro- and macro-infarctions, and also remove donor antigens within the transplant's blood vessels that later could sensitize the recipient. Then through the same needle in the major artery, fill the transplant's blood vessels with heparin solution in about 20,000 I.U./ml concentration, while progressively and quickly clamping at the most distant location, the exiting veins, retaining the 20,000 I.U./ml solution within the artery, the vascular-space of the transplant and the exiting veins. Finally, the transplant can be removed from the donor and put into a plastic sterile bag containing sterile heparin solution, preferably buffered at a pH of about 5.5 and containing about 5,000 I.U./ml concentration, which has been warmed to a constant temperature of 95° F. (35° C.C.) regulated automatically by the electrically-warmed-transporting-blanket, for rapid transport to a recipient.

During surgery the recipient and the transplant are maintained in an acidosis which prevents breakdown of the transplant, and the recipient is heparinized at the conclusion of the surgery by continuous intravenous infusion to prevent initial destruction of the transplanted transplant. After intravenous infusions have been terminated, the patient is maintained in a heparinized condition post-operatively by subcutaneous injections of heparin once or twice daily with about 5,000 to about 20,000 I.U. doses, keeping the laboratory coagulation factors within therapeutic range. This can be carried out in a hospital by health professionals, or at home by the patient or relatives for an extended period of time to minimize organ rejection and enhance physiological function of the transplant(s).

It will be appreciated by those skilled in the art that while present transplant techniques preserve organs at low temperatures, particularly 37° C. that this may not be the optimal storage temperature. The rationale for keeping the organ at low temperature is to inhibit cellular degradative processes. Thus, it will be appreciated that an additional appealing feature of the instant invention is that it is possible to maintain the organ at physiological temperatures, or about 37 degrees Centigrade, because at this temperature the anti-cellular destructive effects of heparin are apparent. Consequently the physician is given a choice of preserving organs at low temperatures, or if this is not desirable, the organ can be maintained at near physiological temperatures.

Related to the preservation of organs is the short term in vitro preservation of tissues for pathological examination, or forensic or other uses. Particularly applicable may be the preservation of tissues for microscopic examination to aid in the evaluation of a particular disease state. Thus, tissues can be removed in a biopsy procedure, treated with heparin without use of chemicals that kill the cells, and then examined microscopically without fear that the examination will reflect the deterioration due to cellular destructive enzymes which could lead to a misdiagnosis. For example, a variety of tumors have associated membrane receptors that are susceptible to degradation once they are removed from the body. Such receptors are often found associated with breasts or ovarian tumors. Using conventional preservation techniques these receptors are often not detectable, consequently the histochemical nature of the patient's cancer is not diagnosed, often with disastrous consequences. Without wishing to be restricted to a particular mechanism, it is thought that heparin or related chemicals facilitate forensic diagnosis by preventing the breakdown and protecting and preserving cells, tissues, etc. for a limited time, so that a more accurate initial determination of the condition or state of the cells, tissue, etc. can be ascertained on gross and microscopic examination or by physical or biochemical determination.

Utilization of heparin to preserve tissues that are to be examining microscopically in medical diagnosis can be achieved by incorporating heparin in an amount of 1,500–5,000 international units per milliliter in a suitable physiologically balanced salt solution and contacting the salt solution onto the tissue, or in other ways immersing the tissue in the solution. This procedure may be used alone or with currently used chemical fixation methods. However, it is probably most suitably used on frozen sectioned biopsy material which is susceptible to cellular degradation in that the resolution afforded by the frozen section technique is negated if the tissue is first subjected to chemical fixation. It will be further appreciated by those skilled in the art that preservation of tissues will also find considerable application in the forensic field.

I will now describe the preferred conditions under which heparin is beneficially employed. The conditions most suited to the two general types of medical applications will be described separately. The first will consist of conditions suited to facilitating wound healing, regardless of whether the wound is on the exterior or interior of an epithelial body surface. The second focuses on the conditions that most effectively retard organ, tissue, or cellular degradation once these are removed from the body.

The first category of treatments, that is, interior or exterior epithelial skin wounds, involves applying to the area of the wound about 1,000–5,000 international units per milliliter of heparin. This concentration is most suited for topical applications wherein heparin is conveniently administered in the form of a solution or a cream or salve. A variety of such creams or salves are well known to those skilled in the art. If heparin is desired to be administered throughout the body to aid internal wound healing, this can be achieved by injecting heparin solution at a concentration of about 10,000–40,000 international units per milliliter and maintaining this dose for several days or until such time as a beneficial result is apparent. I have found that for topical applications of heparin, it is most efficacious to apply the solution in a carrier having an acidic pH and particularly a pH of about 5.5. For reasons that are presently unknown, the medically beneficial uses of heparin are most apparent at acid pH's. Without wishing to be restricted to a particular mode of action of heparin as applicable to the instant invention, it is likely that this pH is favored because heparin interacts with and inactivates molecules involved in an inflammatory reaction, particularly histamine and serotonin and proteolytic enzymes most effectively at acid pH's. Since histamine is known to effect cellular destruction, its inhibition likely facilitates wound healing.

Further medical applications of heparin, hithertofore not known in the art, are similarly premised on the anticellular destructive activity of the molecule. Thus, for example, it is expected that heparin will preserve blood and blood products thereby giving them a longer shelf life than is presently observed. Similarly, cell and tissue injuries due to snake or insect bites, or ingestion of corrosive chemicals will also benefit from heparin application. In these instances, it is anticipated that heparin concentrations of about 1,500–5,000 international units per milliliter will be most efficacious.

As alluded to above, a variety of pharmaceutical carriers can be employed with heparin to realize its beneficial uses. Such can be in liquid, solid or vapor form, and can be applied by injection, dripping, spreading or aerosol. A variety of solid pharmaceutical carriers can be imagined including starch, sugars, talc, manitol and the like. Again, it should be stressed that such compositions preferably have an acidic pH at the site of injury, and particularly a pH of about 5.5. It will be understood that the term carrier is meant to include, in addition to the above, buffered and non-buffered liquid.

It is important to note that for a particular medical application that the precise concentration of heparin that is most beneficial may be determined empirically. That is while concentration ranges are provided herein that are believed to be those that are most useful for a particular application, in many instances these concentrations may not be optimal, and that it may be desirous to have a procedure that can be utilized to determine the optimal heparin concentration.

It will be appreciated by those skilled in the art that there are at least two assays that can be utilized to determine the optimal heparin concentration. The first can be done in a clinical setting and relies on ascertaining the immediate physiological changes caused by heparin. These are relief from pain, inflammatory erythema blanching and cessation of wound weeping. Cessation of pain and inflammatory erythema blanching occurs within minutes of heparin application, and thus gives a ready indication of whether a suitable concentration of heparin is being utilized. Cessation of wound weeping occurs approximately 6 to 24 hours after treatment and serves as a further indication that the proper amount of heparin is being utilized. In addition, other indicators that an appropriate amount of heparin is being applied is that the wound site undergoes revascularization and regranulation. These events occur later in time than the prior events, and thus act as a correlative check to insure that the proper amount of heparin is being employed. It will be apparent that based on both subjective doctor-patient communications and objective observations by the physician that an empirically useful concentration of heparin can be determined for a particular application.

It will be appreciated that while the minimally effective dose of heparin can be determined by the above methods, that consideration should also be given to insure that an excessive amount of heparin is not administered. An excessive amount of heparin is that which no longer has medically beneficial uses, and has significant anti-blood clotting activity. The latter is readily ascertainable by monitoring a patient's clot time. Generally clot times of $1\frac{1}{2}$–2 times longer than normal indicate that excessive doses of heparin are being used. Thus, by monitoring the above parameters of pain, erythema blanching, etc. and clotting time, the lower and upper limits of heparin concentration can be ascertained.

A second procedure is based on determining the amount of histamine present at a particular wound site or that is associated with the cellular destructive processes ongoing in organs or tissues that have been removed from a donor prior to transplantation or microscopic examination respectively. The procedure involves measuring the amount of heparin needed to inactivate histamine present as a result of cellular injury and consist of extracting histamine from the subject tissues or organs and titrating it against heparin. Such procedures are well known to those skilled in the art. Also the reaction conditions for titrating a particular amount of heparin needed to inactive histamine concentrations in biological fluids and tissues are also well known. Particularly it is known that at a pH of about 5.5, one milligram of histamine binds to approximately 400 units of heparin. This relationship enables a determination of approximately how much histamine is present in the subject tissues or organs and consequently how much heparin should be used.

The invention is described below with reference to particular examples. However, it will be understood by those skilled in the art that the invention is not limited to either the materials or methods described in these examples. It will be particularly apparent that the applications of heparin and related molecules are not restricted to humans but can be applied to treating animals suffering from similar bodily disorders. Moreover, it will be readily apparent that there are numerous substitutions as to both the materials and methods that can be easily imagined and that will substitute equally well for the materials and methods described.

It will be further appreciated by those skilled in the art that while the mechanism by which heparin exerts its myriad effects is not known, it is nevertheless apparent that it maintains, promotes and protects vital cellular functions. Consequently it is to be anticipated that in addition to the uses described below, heparin will be found to have other related uses. Moreover, as shown in some of the examples, heparin is also capable of enhancing as well as preserving and restoring cellular functions. Thus it is apparent that heparin is a key medicament with a truly wide range of medical uses and that it is the intent of this patent that applications of heparin based on its above-described properties are to be considered within the scope of this patent.

EXAMPLE I

CAESAREAN INCISION CELLULITIS AFTER ABSCESSED DEHISCENCE

A 30 year old female displaying an abscess-pocketed cellulitis resulting from complications of a Caesarean section and that extended across most of the incision was treated with heparin. Prior to treatment the lesion was infected, ischemic, necrotic and widely patent and it had a purulent pungent odor. FIG. 1A. The lesion was 13.5 cm long and 2.5 cm in depth (average). Heparin was administered subcutaneously in a 20,000 I.U. dose. After some purulent semi-liquid material was gently wiped out, 40,000 I.U. of heparin was sprayed onto the necrotic infected walls. Then, after a thin plain sterile gauze pack was inserted, an additional 60,000 I.U. of heparin was slowly applied to the gauze within the lesion. A single layer of Telfa pad dressing was applied and taped to the abdominal wall at only three spots along the superior margin of the Telfa pad. Oral Ultracef was started in a 500 mg twice daily dose. Heparin treatment relieved the pain and it did not recur.

Six hours later, there were faint traces of blood on the gauze packing, and the surfaces of the lesion had the erythematous rubor of early revascularization. FIG. 1B. The purulent exudate observed six hours earlier had not returned and the previous pungent odor was not present. FIG. 1B. Slowly and repeatedly, over a twenty-minute period, the 5,000 I.U./ml heparin solution was applied topically, 20,000 I.U. prior to, and 40,000 I.U. after, reinserting a new thin gauze packing.

The next day, at 24 hours after the onset of heparin treatment, the Telfa bandage was stained with dried clear secretions and reddish blood. The gauze packing was blood-ringed. FIG. 1C. The walls of the lesion were more erythematous and revascularized, showed areas of early granulation between areas of whitish fibrous tissue. FIG. 1C. Overall there was much less infection and no pungent odor. The patient had no pain. Then heparin solution was administered, 15,000 I.U. subcutaneously and 75,000 I.U. topically (40,000 I.U. prior to and 35,000 I.U. after reinsertion of the thin gauze packing). The thin Telfa dressing was changed twice daily, by physician or, at home, by her husband.

Starting day 2, at home, the patient's husband added topical heparin solution to the dehisced incision and the gauze two or more times a day, including when he changed the gauze once or twice a day. The total daily heparin dose applied by the husband was 25,000 I.U. for 3 days, then 20,000 I.U. for 15 days, then 10,000 I.U. for 2 days. In the office an additional 205,000 I.U. of heparin solution was applied topically into final healing, or approximately 20,000 I.U. daily on those days when it was added. Thus the total heparin, administered topically by the physician and by the husband, day 1 through day 22, was 732,000 I.U. Some topically-applied heparin promptly drained out before, theoretically, it could be efficiently utilized. With slower administration, a lesser amount of topical heparin might be as effective.

Heparin was administered subcutaneously once a day by the physician in the office or by the husband at home. The subcutaneous dose was 20,000 I.U. daily, treatment days 1, 3, 5–16; and 10,000 I.U. daily, treatment days 17–22. The dose on day 2 was 15,000 I.U. The patient's husband administered the injections of heparin at home on treatment days 8, 9, 12–16, 18–21, and 22. The total parenteral heparin dose days 1–22 was 365,000 I.U.

On day 11, 22 hours after 20,000 I.U. of heparin was administered subcutaneously and 40,000 I.U. had been applied topically, the Coagulation Panel values were normal: Bleeding Time 4 minutes; Prothrombin Time 12, Control 12; ACTIVATED Partial Thromboplastin Time 27, Control 28; and Platelet Count 227,000. Coagulation was not altered by these doses of heparin.

The dehisced incision progressively revascularized, granulated in, closed and healed by re-epithelialization along the incision skin surface, without complications, on the 29th day of treatment. Photograph 2D shows the incision on treatment day 8.

The dehisced incision was widely patent and measured 13.5 cm in length and 2.5 cm in depth (average) when first observed. Treatment day 5, the depth was 2.4 cm. The length was 11.25 cm and the depth was 1.8 on treatment day 7. On treatment day 10, the length was 10.0 cm and the depth was 1.1 cm. By the 17th day of treatment the length was 9.0 cm and the depth was 0.7 cm. On day 23 the depth was 0.2 cm. The lesion was closed day 29.

Thus, an ischemic necrotic infected dehisced Caesarean-section transverse suprapubic incision in a 30 year old woman that had not responded to standard conventional treatment was healed by three weeks of daily topical heparin applied several times a day and once daily subcutaneous heparin injections in 20,000 I.U. or 10,000 I.U. doses and oral cephalosporins. No other medical or surgical treatment was necessary.

EXAMPLE II

NECROTIC INFECTED WEEPING WOUND OF FOREARM

A 54 year old woman injured her left forearm in a water-skiing accident. The 5.1 by 5.6 cm wound, which was partially an abrasion and partially an avulsion of the skin on the dorsal surface, became infected. One physician she consulted had advised her to keep it moist with applications of nitrofuradantin ointment. Three days later, a second physician had prescribed oral Penicillin-VK and an unknown topical ointment to dry the weeping infected lesion. Neither treatment had been effective.

The 5.1 by 5.6 cm necrotic, purulent, avascular surface lesion surrounded by an area of inflammatory erythema on the left forearm was treated with heparin as follows. First, 10,000 I.U. of heparin was injected into subcutaneous abdominal fat. Topical heparin, 4 ml of 5,000 I.U./ml concentration, was slowly dripped onto the purulent necrotic wound over a ten-minute period of time. After waiting another 10 minutes to allow full exposure of the heparin to the wound, the area was loosely bandaged with a dry nonadhering sterile Telfa pad. An additional quantity of heparin was sprayed on and soaked through the Telfa pad directly over the wound. The patient was given dicloxacillin 250 mg, four times daily. Seven hours later, the Telfa pad was removed and, with it, a quantity of purulent material. The same treatment with topical heparin was repeated.

The next morning, 24 hours after heparin treatment was started, the wound was clinically 90% free of infection. There was increased blood flow within the wound and there was no surrounding inflammatory erythema. There was evidence of early granulation. Heparin subcutaneous dose was 10,000 I.U. and heparin topical dose was 2 ml of the 5,000 I.U./ml solution. Telfa pad dressing and oral dicloxacillin were continued. The next day, 48 hours after initiating treatment, the wound was estimated to be 50% well and rapid re-epithelialization was in progress. Heparin was used topically, in 5,000 I.U. doses, for the last time. Twelve days after heparin treatment was initiated, there was new pink-colored skin over the entire area. No contractures developed. The new skin was only partially pigmented, but it was cosmetically pleasant.

EXAMPLE III

POSTOPERATIVE CELLULITIS WITH ABSCESS-SINUS TRACT

A 66 year old male displaying cellulitis involving the posterior lower third of his right leg, and having within the area of the cellulitis an abscess sinus tract was treated with heparin. The opening of the tract was 20 mm above the calcaneus insertion of the achilles tendon. The abscess sinus tract extended up into the leg along the achilles tendon, of which a thinned-down segment was visible within the ostia and sinus. The ostia was 30 mm in vertical diameter and the tract was 97 mm in length. The greyish walls of the tract and ostia surface edges were avascular and necrotic and covered with a purulent and pungent weeping fluid exudate. The purulent and pungent fluid was draining persistently from the ostia. FIG. 2A. It is important to note that this patient had been treated for five months prior to heparin treatment using surgical debridement, oral and topical antibiotics and twice daily soaks without effect.

Heparin treatment was started midmorning, with 20,000 I.U. heparin injected into subcutaneous abdominal wall fat and 4 ml of the 5,000 I.U./ml heparin solution (a total 20,000 I.U.) was slowly and repeatedly applied topically so that the heparin was placed within the abscess tract to rinse the wound; the heparin was dripped on the ostia opening; and finally, the heparin was used to saturate a sterile gauze packing tape that was inserted within the draining abscess tract. Oral antibiotics, dicloxacillin 500 mg, twice daily, and Geocillin 382 mg, three times a day, were continued by mouth. A sterile dry nonadhering Telfa pad was applied. Soaking of the leg in water or in antimicrobial water solution was discontinued.

Eight hours later, there was an increased vascular-type rubor color to the skin of the upper areas of the cellulitis, and less swelling of the ankle and foot. There were faint traces of blood on the tape and at the ostia and less drainage from the sinus tract. Treatment consisted of the topical administration of heparin, including reinsertion of the heparin solution-soaked packing tape within the sinus tract.

The next morning, 22 hours after the initial heparin treatment, the Telfa pad dressing and the gauze-tape sinus packing were soaked with a serous, pinkish, blood-tinged fluid. FIG. 2B. The drainage from the abscess sinus tract was less and it was nonpungent and less purulent in nature. There was less tissue swelling and more rubor color to the skin of the ankle and heel.

Heparin was administered: 20,000 I.U. subcutaneously and a total 20,000 I.U. topically, within and on, the abscess sinus tract and onto the tape placed within the tract. The tape was less deeply replaced. Subsequently, as the sinus tract filled in, the gauze tape packing was replaced progressively less deeply. At 32 hours, 10,000 I.U. of heparin was topically applied.

The following morning, 46 hours after initiating heparin therapy, the swelling had subsided to the extent that the medial malleolus of the tibia was then prominent. Normal skin rubor had returned to the ankle, signalling a more normal blood flow. Traces of bright red blood were on the packing that had been within the tract. Overall, there was essentially minimal drainage, and it was not pungent or purulent. Subcutaneous heparin injection was 10,000 I.U., and 5,000 I.U. of heparin was applied topically and repeated again at 56 hours.

The next morning, 72 hours after heparin treatment was started, the swelling was reduced by 40%. Portions of the tape had dark red-colored blood. The length of the abscess tract was reduced from 97 mm to 50 mm. There was very little drainage. The skin blood supply on both sides of the ankle was vastly improved, as evidenced by the skin rubor and the prominent veins. The same doses of parenteral and topical heparin were again applied. Cultures of the sinus tract were taken and, after 48 hours, were reported to be negative for bacterial or fungal growth.

Treatment with parenteral heparin, 10,000 I.U., was given the next 4 days, then discontinued for 8 days. Topical heparin was continued, with daily reduction in dose, into final healing.

Figure 2D:
Figure 2A:
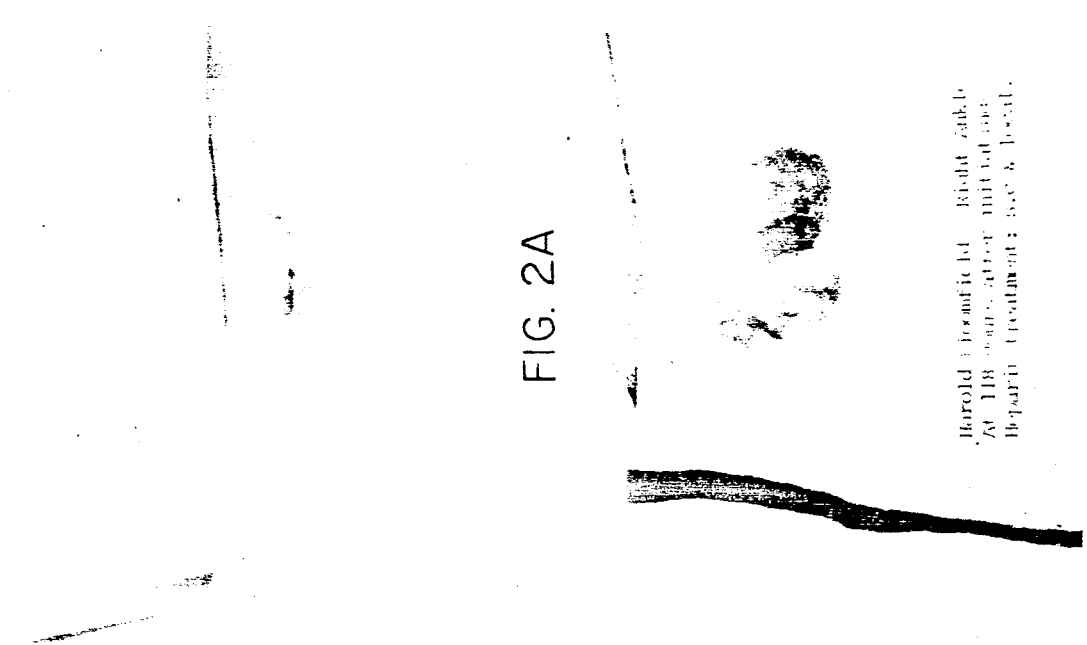
Figure 2C:
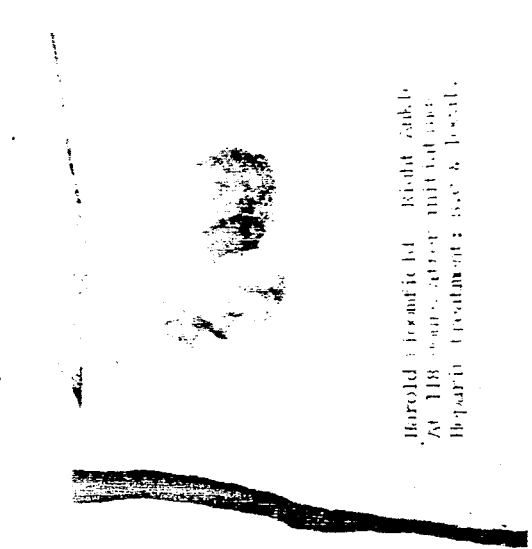

At 118 hours, the reduced length of the packing tape is shown in FIG. 2C, and the 60% reduction in swelling in FIG. 2D. The sinus tract was progressively filling in, and the ostia was circumferentially being reduced in size by vascular granulation tissue. FIG. 2D.

The packing tape was less deeply replaced, and was no longer required after the sixth day, as the tract had granulated in, and was then only a shallow depression within the ostia. The ostia also was rapidly reducing in size. But, for unknown reasons, healing of the ostia opening required more days than the filling in of the cellulitis-abscess-sinus tract. Surface closure healing with heparin apparently awaited complete deep healing.

Fifteen days after treatment was started, when the ostia was almost 90% closed, the patient was seen by a plastic surgeon in the latter's office, for an appointment made prior to the starting of heparin treatment. Unaware of the heparin therapy, the plastic surgeon, without warning, surgically debrided the lesion widely in the area of the nearly healed ostia. Blood promptly flooded from the freshly denuded area, attesting to the abundant revascularization that had taken place. The plastic surgeon's intent was to remove surface epithelium so that it would not cover over, before deep healing had been completed. Without prior knowledge of heparin's effects, the plastic surgeon had not recognized that the sinus tract had already healed fully and that no surface debridement was necessary at that point. Because he had expected a relatively avascular response, he was surprised and apologetic. FIG. 2F shows the ostia area 4 days after the office surgery. Unhappily, the skin surface healing was disrupted and delayed. Complete healing of the lesion that was expected in less than a month, required several weeks more to re-epithelialize and become full-thickness skin. FIG. 2G shows the lesion a month later.

Following this surgical debridement, parenteral heparin was started again, with 10,000 I.U. administered subcutaneously daily for 8 days. Topical heparin was administered in diminishing amounts until full re-epithelialization was evident. The healing progressed slowly and smoothly into final healing without further complications. Full functional use of the leg and foot were possible when the wound was healed, and the cosmetic result was pleasant in appearance. FIG. 2H shows the leg three years later.

EXAMPLE IV

CERVICAL CELLULITIS WITH HYPOPHARYNX TO SKIN FISTULA

A 55 year old male suffering from complications due to a laryngectomy was treated with heparin. The complications consisted of a cellulitis and a fistulous tract from his hypopharynx extending out the right side of his neck. The cellulitis did not respond to treatment with antibiotics, and the fistulous tract did not respond to cauterization with silver nitrate, which was performed prior to heparin treatment by a surgeon five times. With every deglutition, masticated food and oral fluids exited via the fistula. The fistulous tract progressively enlarged.

Topical treatment with heparin was initiated by a physician, and continued after the first day by a registered nurse. Every 6 hours, topical heparin solution was placed within the fistulous tract until it was full. Liquid erythromycin in a 250 mg per 5 ml dose was given via a nasogastric tube every 6 hours. A dry sterile Telfa pad was applied over the fistula ostia. No gauze packing was placed within the fistulous tract. No additional medical treatment was given and there was no further surgical treatment.

The fistulous drainage became progressively less and the previous purulent pungent discharge was replaced by a scant clear fluid, which was occasionally tinged with a trace of blood. The swelling and doughy consistency of the neck were progressively reduced and replaced by normal pink firm tissue into the final healing phase. The greyish necrotic surfaces of the fistula revascularized, granulated and the ostia re-epithelialized progressively into final healing. The fistulous tract healed from the inside out, and only in the final phase of healing did it close on the surface. After 11 days of topical heparin use, and the day heparin treatment was stopped, the external ostia was re-epithelialized with a thin layer of cells. Thereafter, the epithelium progressively thickened into normal thickness skin. No surface contractures developed. No local or systemic bleeding occurred. No pain medication was required.

EXAMPLE V

PYODERMA-CELLULITIS IN A PRETIBIAL LACERATION

A 69 year old female presenting torn skin of the left leg above the tibia resulting from injury to a subcutaneous hematoma was treated with heparin. Heparin solution was applied twice daily to the infected, weeping, necrotic wound, by the physician in the office or by the patient at home, for 12 days. Day 1, topical heparin dose was 20,000 I.U., twice daily; reduced progressively to 2,500 I.U., twice daily, on day 12. Heparin, in 10,000 I.U. dose, was parenterally administered by injection into subcutaneous fat, once daily for 3 days.

The wound revascularized, granulated, re-epithelialized and healed slowly. Antibiotics were discontinued after 18 days. A scab formed over the wound. The scab fell off the fully healed area four weeks after heparin therapy was initiated. No skin contractures developed and the cosmetic result was pleasant.

EXAMPLE VI

MOTORCYCLE ACCIDENT "ASPHALT BURNS" ARM, LEG, AND BODY

A 19 year old male having extensive asphalt "burns," abrasions and irregular skin avulsions of his right upper and lower extremity, flank, and hip resulting from a motorcycle accident was treated with heparin. Topical heparin solution, 8 ml of 5,000 I.U./ml concentration, was sprayed onto the "burns" twice daily, for 3 days; and 10,000 I.U. was subcutaneously injected into fat, once daily, for 3 days. Erythromycin was orally administered in 250 mg dose, 4 times a day. Telfa dressings were applied, and soaked off, when removed.

The heparin solution relieved the pain. The deep irregular abrasions and the area where skin had been avulsed stopped weeping, revascularized, granulated, reepithelialized and healed without contractures in 12 days. The skin was comfortable and cosmetically pleasant, although some areas have no skin pigment.

EXAMPLE VII

HEALING OF ABRASION-AVULSION OF PALM SKIN

A 40 year old male, injured in a motorcycle accident and suffering from asphalt-pavement "burn" abrasions and avulsion of his right hand palm skin was treated with heparin. The initial topical dose of heparin was 20,000 I.U.; then 5,000 I.U. or less, twice daily, for ten days, with heparin dose reduced or discontinued in revascularized areas where bleeding could occur if heparin were continued.

The pain in the wound was relieved promptly by the topical application of the heparin. The wound was smaller, drier, and nonpainful one day after heparin was started. The wound revascularized, granulated, re-epithelialized and was healed 3 weeks post-accident. FIGS. 3A-D show the palm, prior to heparin, after 1 and 4 days of heparin topical treatment, and healed on day 22.

EXAMPLE VIII

KNEE SKIN ABRASION-AVULSION CELLULITIS

A 20 year old male suffering from a knee injury was treated with heparin. Treatment consisted of parenteral and topical heparin, dry nonadhering dressings and oral antibiotics. Subcutaneous heparin dose was 20,000 I.U. daily, for 2 days, and 10,000 I.U., for 1 day. Topical heparin dose was 20,000 I.U., initially, and 10,000 I.U., twice daily, reduced, progressively to 2,500 I.U., for 35 days. Antibiotics were erythromycin, 500 mg, twice daily, for 2 days; then Keflex 500 mg, four times daily, for 4 days; then Tegopen 500 mg, three times a day, for 10 days; then erythromycin, 500 mg, twice daily, for 7 days; and finally, Ultracef 500 mg, twice daily, for 3 days.

Figure 4B:
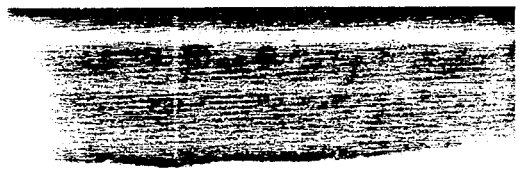
Figure 4C:
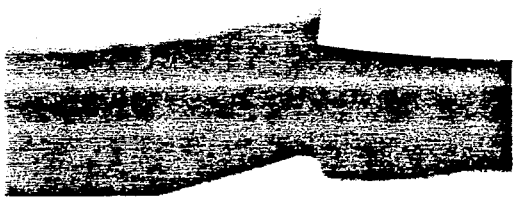
Figure 4A:

Healing progressed slowly and unevenly through revascularization, granulation, and epithelialization of concentrically reducing circular areas. The cosmetic and functional results were good. FIGS. 4A-C show the lesion, treatment days 1 and 41, and two years later.

EXAMPLE IX

NECROTIC WEEPING DERMATITIS OF LIP

A 70 year old male, presenting a persisting necrotic weeping dermatitis of the lower lip, was treated with heparin. The lip lesion, which had been resistant to all treatment by a dermatologist, was healed within 5 days after topical heparin was started. Heparin was dripped onto the lip, four or more times a day; and 10,000 I.U. units, applied in divided dose, were used daily for 3 days. No dressings were used. There was no other treatment. Lip pain and itching subsided and stopped. The weeping from the white necrotic surface stopped. The lip revascularized and rapidly re-epithelialized, without contracture. When healed, the lip was cosmetically normal.

EXAMPLE X

NONHEALING BYPASS-VEIN-DONOR-SITE IN A DIABETIC

Figure 5A:

An 81 year old diabetic with ischemic heart disease and chronic angina displaying a superficial saphenous vein donor-site wound of his left lower extremity below the knee resulting from coronary artery bypass surgery was treated with heparin. Previously, four months of conventional treatment, the incision site medial to the tibia in the midleg was open, weeping, ischemic and purulent. FIG. 5A.

Figure 5B:
Figure 5C:

Topical heparin solution, 10,000 I.U., initially, and 2,500 I.U., applied twice daily, for 29 days, resulted in revascularization and scab closure of the lesion. After 4 days of heparin the lesion was smaller, nonweeping, revascularizing and much less purulent. FIG. 5B. After 23 days of topical heparin use, healing was unusually slow compared with other lesions of similar size treated with topical heparin. The patient showered daily, thus exposing it to shower water daily. The patient was advised to keep the lesion dry, and thereafter the healing increased, with a scab covering the lesion on day 29 of heparin therapy. Erythromycin, then Augmentin, and dicloxacillin were given orally, 250 mg, 4 times daily. FIGS. 5A-B show this early heparin healing phase.

Figure 5D:
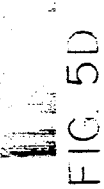

Thirty-three days later, the very thick scab that was still adherent, and which became repeatedly wet when he resumed daily showering without covering it, was removed. An incompletely healed, purulent base was revealed. FIG. 5D. Topical heparin was started again. Twice-daily application of less than 2,500 I.U. daily accelerated and completed the healing. FIGS. 5D show the lesion after 6 days of topical heparin.

In this case, heparin was used in both an early and in a late healing phase. In the early phase, heparin increased revascularization-granulation-re-epithelialization. In the late phase of healing, heparin increased re-epithelialization.

It will be understood by those skilled in the art that the above examples of the instant invention are provided as representative of the many hithertofore unknown medically beneficial therapeutic uses of heparin, or chemically related molecules, and should not be construed as limiting the invention. It will be appreciated that numerous other such applications are anticipated and fall within the scope of the amended claims.

We claim:

1. A method for treating a patient having a lesion selected from the group consisting of circumcisions, injuries due to cold temperature exposure, fissures, fistulas, keloids and non-healing open necrotic ischemic skin lesions which comprises administering to said patient, at an acidic pH and for a time sufficient to effect treatment of said lesion, a pharmaceutically acceptable agent consisting essentially of an anticellular destructive chemical selected from the group consisting of heparin, heparinoids and heparin sulfate.

2. A method as in claim 1 wherein the adequacy of progress of initial treatment is indicated by termination of acute pain incurred by said patient from said lesion.

3. A method as in claim 1 wherein said agent is administered onto the surface of the affected organ at the site of said lesion.

4. A method as in claim 3 wherein said agent is administered 1-4 times per day in a concentration of 1,500-5,000 International Units per milliliter.

5. A method as in claim 1 wherein said agent is administered subcutaneously into normal non-involved subcutaneous fat tissue.

6. A method as in claim 5 wherein said agent is administered in a concentration of 5,000-80,000 International Units per milliliter.

7. A method as in claim 1 wherein said non-healing open necrotic ischemic skin lesion is a skin ulcer.

8. A method as in claim 7 wherein said skin ulcer is a decubitus ulcer.

9. A method as in claim 7 wherein said agent is administered topically to said skin ulcer.

10. A method as in claim 9 wherein said agent is administered in a concentration of 1,500-5,000 International Units per milliliter.

11. A method as in claim 1 wherein said injury due to cold temperature exposure is hypothermic injury or frostbite.

12. A method as in claim 11 wherein said agent is administered subcutaneously at the time of acute exposure.

13. A method as in claim 12 wherein said agent is administered in a concentration of 5,000-80,000 International Units per milliliter.

14. A method as in claim 11 wherein said agent is administered intravenously during later warming and thawing.

15. A method as in claim 14 wherein said agent is administered in a concentration of 5,000-20,000 International Units per milliliter.

16. A method as in claim 14 wherein the intravenous agent is administered at a rate sufficient to relieve the acute pain of said patient incident to said warming and thawing.

17. A method as in claim 16 wherein said administration is terminated when said pain is completely relieved.

18. A method as in claim 1 wherein said lesion is circumcision and said agent is administered to the circumcised penis prepuce.

* * * * *